United States Patent
Kang et al.

(10) Patent No.: US 10,111,596 B2
(45) Date of Patent: Oct. 30, 2018

(54) BLOOD PRESSURE MEASURING APPARATUS AND METHOD OF OPERATING THE SAME

(71) Applicant: SAMSUNG ELECTRONICS CO., LTD., Suwon-si (KR)

(72) Inventors: Jae Min Kang, Seoul (KR); Yong Joo Kwon, Yongin-si (KR); Sun Kwon Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 85 days.

(21) Appl. No.: 15/174,346

(22) Filed: Jun. 6, 2016

(65) Prior Publication Data

US 2016/0360981 A1 Dec. 15, 2016

(30) Foreign Application Priority Data

Jun. 12, 2015 (KR) .................. 10-2015-0083617

(51) Int. Cl.
*A61B 5/021* (2006.01)
*A61B 5/00* (2006.01)
*A61B 5/024* (2006.01)

(52) U.S. Cl.
CPC ...... *A61B 5/02125* (2013.01); *A61B 5/02416* (2013.01); *A61B 5/681* (2013.01); *A61B 5/6803* (2013.01); *A61B 5/7278* (2013.01); *A61B 5/742* (2013.01); *A61B 2560/0475* (2013.01); *A61B 2560/0487* (2013.01); *A61B 2562/043* (2013.01)

(58) Field of Classification Search
CPC .. A61B 5/02438; A61B 5/02125; A61B 5/681
See application file for complete search history.

(56) References Cited

U.S. PATENT DOCUMENTS

| | | | |
|---|---|---|---|
| 2003/0153824 A1* | 8/2003 | Tsubata ............... | A61B 8/4227 600/407 |
| 2010/0210956 A1 | 8/2010 | Im | |
| 2013/0079648 A1* | 3/2013 | Fukuzawa .......... | A61B 5/02125 600/500 |
| 2014/0051941 A1* | 2/2014 | Messerschmidt .... | A61B 5/6898 600/301 |
| 2014/0114201 A1 | 4/2014 | Watanabe et al. | |

FOREIGN PATENT DOCUMENTS

| | | |
|---|---|---|
| JP | 8-299290 A | 11/1996 |
| JP | 2000-107141 A | 4/2000 |
| JP | 3721410 B2 | 11/2005 |
| JP | 2012-211864 A | 11/2012 |
| JP | 2014-83122 A | 5/2014 |
| KR | 10-1068116 B1 | 9/2011 |

* cited by examiner

*Primary Examiner* — Michael Kahelin
(74) *Attorney, Agent, or Firm* — Sughrue Mion, PLLC

(57) ABSTRACT

A blood pressure measuring apparatus and a method of operating the same are provided. The blood pressure measuring apparatus includes: a strap; and a main body that is rotatably connected to the strap, wherein the main body includes: a first pulse wave measurer configured to measure a first pulse wave; a second pulse wave measurer that is spaced apart from the first pulse wave measurer at a regular interval and is configured to measure a second pulse wave; and a blood pressure measurer configured to analyze the first pulse wave and the second pulse wave and determine a blood pressure based on the analyzed first pulse wave and the analyzed second pulse wave.

9 Claims, 7 Drawing Sheets

BLOOD PRESSURE MEASURING APPARATUS AND METHOD OF OPERATING THE SAME

CROSS-REFERENCE TO RELATED APPLICATION

This application claims priority from Korean Patent Application No. 10-2015-0083617, filed on Jun. 12, 2015 in the Korean Intellectual Property Office, the disclosure of which is incorporated herein by reference in its entirety.

BACKGROUND

1. Field

Apparatuses and methods consistent with exemplary embodiments relate to a blood pressure measuring technology.

2. Description of the Related Art

With a growing interest in personal health, various types of biometric information detection devices are being developed, and devices specifically designed for healthcare are being developed with the widespread use of various wearable devices that may be directly worn by subjects.

A cuff-less blood pressure sensor is a blood pressure sensor of an indirect measurement method, in which blood pressure is measured by a Pulse Transit Time (PTT) method using an optical signal and an electrocardiogram (ECG) signal, or by a Pulse Wave Analysis (PWA) method that analyzes pulse waves based on an optical signal.

However, the PTT method is cumbersome in that touches of both hands are required, and an ECG signal is further needed in addition to a pulse wave signal. The PWA method, which analyzes only a waveform of pulse waves, may not enable accurate blood pressure measurement.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided a blood pressure measuring apparatus including: a strap; and a main body that is rotatably connected to the strap, the main body including: a first pulse wave measurer configured to measure a first pulse wave; a second pulse wave measurer that is spaced apart from the first pulse wave measurer and is configured to measure a second pulse wave; and a blood pressure measurer configured to analyze the first pulse wave and the second pulse wave and determine a blood pressure based on the analyzed first pulse wave and the analyzed second pulse wave.

The main body may be detachably connected to the strap.

The main body may be configured to rotate in a range between 180 degrees and zero degree.

The first pulse wave measurer may be disposed on a side end of a bottom surface of the main body, and the second pulse wave measurer may be disposed on another side end of the bottom surface of the main body.

The blood pressure measuring apparatus may be a wristwatch wearable device.

Each of the first pulse wave measurer and the second pulse wave measurer may be configured to emit light to a subject that reflects the light. The first pulse wave measurer may be configured to sense the light reflected from the subject to measure the first pulse wave, and the second pulse wave measurer may be configured to sense the light reflected from the subject to measure the second pulse wave.

The blood pressure measurer may include: a feature point extractor configured to extract a first feature point from the first pulse wave and a second feature point from the second pulse wave, the second feature point corresponding to the first feature point; and a blood pressure calculator configured to determine the blood pressure based on the first feature point and the second feature point.

The blood pressure calculator may determine a pulse wave velocity between the first feature point and the second feature point, and determine the blood pressure based on the determined pulse wave velocity.

The blood pressure calculator may determine the pulse wave velocity by determining a time difference between the first feature point and the second feature point, and by dividing a distance between the first pulse wave measurer and the second pulse wave measurer by the determined time difference.

According to an aspect of another exemplary embodiment, there is provided a method of operating a blood pressure measuring apparatus that includes a strap and a main body that is rotatably connected to the strap, the method including: sensing rotation of the main body; measuring a first pulse wave by a first pulse wave measurer that is disposed on the main body; measuring a second pulse wave by a second pulse wave measurer that is spaced apart from the first pulse wave measurer and disposed on the main body; analyzing the first pulse wave and the second pulse wave; and determining a blood pressure based on the analyzed first pulse wave and the analyzed second pulse wave.

The main body may be detachably connected to the strap.

The sensing the rotation may include sensing a degree of rotation of the main body in relation to the strap. The measuring the first pulse wave and the measuring the second pulse wave may be initiated in response to the sensed degree of rotation being approximately 90 degrees.

The first pulse wave measurer may be disposed on a side end of a bottom surface of the main body and the second pulse wave measurer may be disposed on another side end of the bottom surface of the main body.

The blood pressure measuring apparatus may be a wristwatch wearable device.

The measuring the first pulse wave may include: emitting light to a subject by the first pulse wave measurer, the light being reflected by the subject; sensing the light reflected from the subject; and measuring the first pulse wave from the sensed light.

The determining blood pressure may include: extracting a first feature point from the first pulse wave; extracting a second feature point from the second pulse wave, the second feature point corresponding to the first feature point; and determining the blood pressure based on the first feature point and the second feature point.

The determining blood pressure may include: determining a pulse wave velocity based on the first feature point and the second feature point; and determining the blood pressure based on the determined pulse wave velocity.

The determining the pulse wave velocity may include: determining a time difference between the first feature point and the second feature point; and determining the pulse wave velocity by dividing a distance between the first pulse wave measurer and the second pulse wave measurer by the determined time difference.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1A:
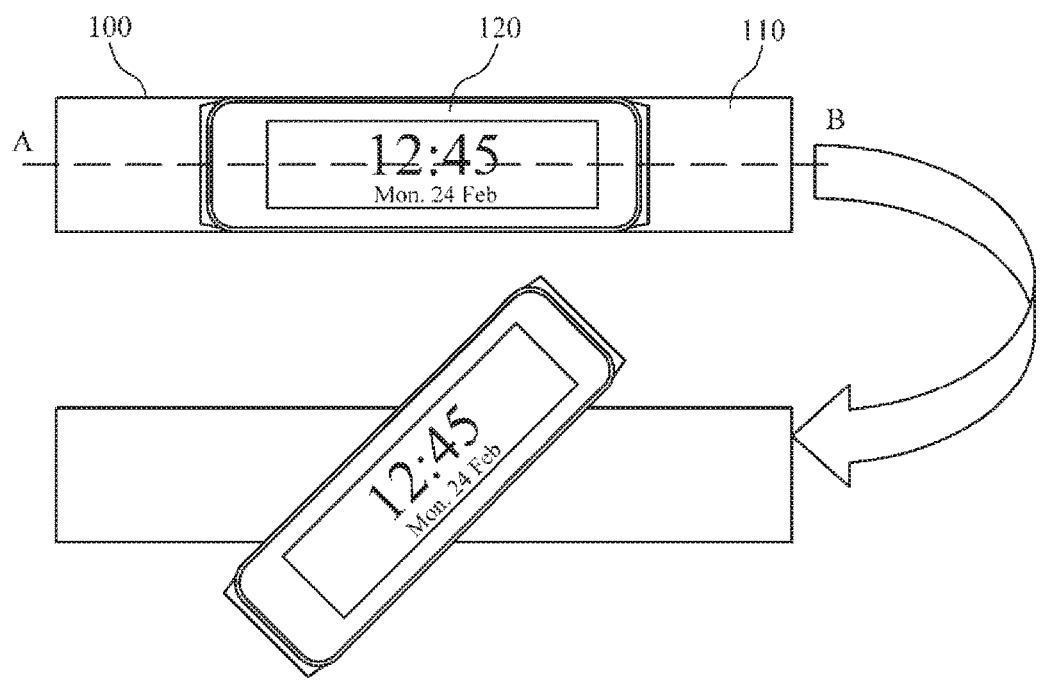
FIG. 1A is a plan view of a blood pressure measuring apparatus.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Figure 1B:
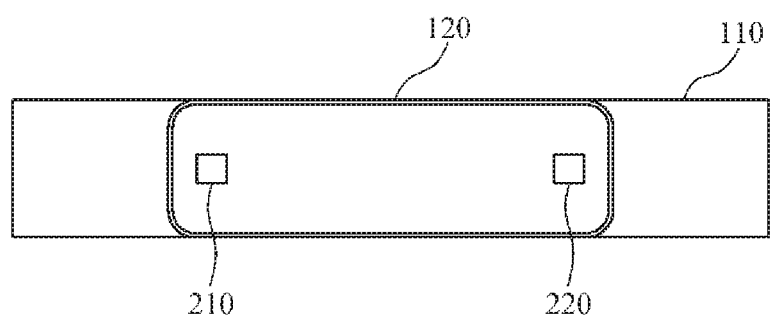
FIG. 1B is a bottom view of the blood pressure measuring apparatus.
Figure 1C:
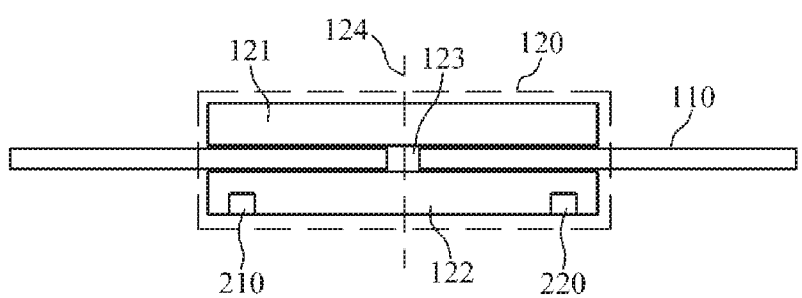
FIG. 1C is a cross-sectional view taken along line A-B of FIG. 1A.

FIG. 1A is a plan view of a blood pressure measuring apparatus. FIG. 1B is a bottom view of the blood pressure measuring apparatus. FIG. 1C is a cross-sectional view taken along line A-B of FIG. 1A.

The blood pressure measuring apparatus 100 may measure blood pressure of a subject in a non-invasive manner. For example, the blood pressure measuring apparatus 100 is a cuff-less type blood pressure measuring apparatus, which measures blood pressure by emitting light on a subject, i.e., a body part of a user wearing the blood pressure measuring apparatus 10, measuring pulse waves by sensing reflected or diffused light, and analyzing the measured pulse waves.

Referring to FIGS. 1A to 1C, a main body 120 of the blood pressure measuring apparatus 100 is rotatably connected to a strap 110. For example, as illustrated in FIG. 1C, an upper portion 121 and a lower portion 122 of the main body 120 are connected to each other by a connection member 123, and the main body 120 is connected to the strap 110 by the connection member 123, such that the main body 120 may rotate 180 degrees or less about a center axis 124. However, the main body 120 is not limited thereto, and may be configured to rotate about other positions (e.g., both ends of the main body, etc.) than the center axis.

Further, the main body 120 may be detachably connected to the strap 110.

The blood pressure measuring apparatus 100 may be a wearable device to be worn on a subject. For example, the blood pressure measuring apparatus 100 may be a wristwatch type, a bracelet type, or a wristband type. However, the blood pressure measuring apparatus 100 is not limited thereto, and may be a ring type, a glasses type, a hairband type, and the like.

Two pulse wave measurers 210 and 220, which are spaced apart from each other, may be disposed on a bottom surface of the main body 120. Although two pulse wave measurers 210 and 220 are illustrated, but the present embodiment is not limited thereto, and three or more pulse wave measurers may be provided according to usage and purpose of a system.

In the case where the blood pressure measuring apparatus 100 is a wristwatch type wearable device, the blood pressure measuring apparatus 100 may be used as a watch in ordinary times, and when measuring blood pressure, the blood pressure measuring apparatus may be positioned over the radial artery of a human's wrist and may rotate 90 degrees. In response to a user's instruction to measure blood pressure, the blood pressure measuring apparatus 100 measures pulse waves at two points, which are spaced apart by a certain distance, by using the two pulse wave measurers 210 and 220 disposed on the bottom surface of the main body 120, and blood pressure may be measured based on the measured pulse waves.

Figure 2:
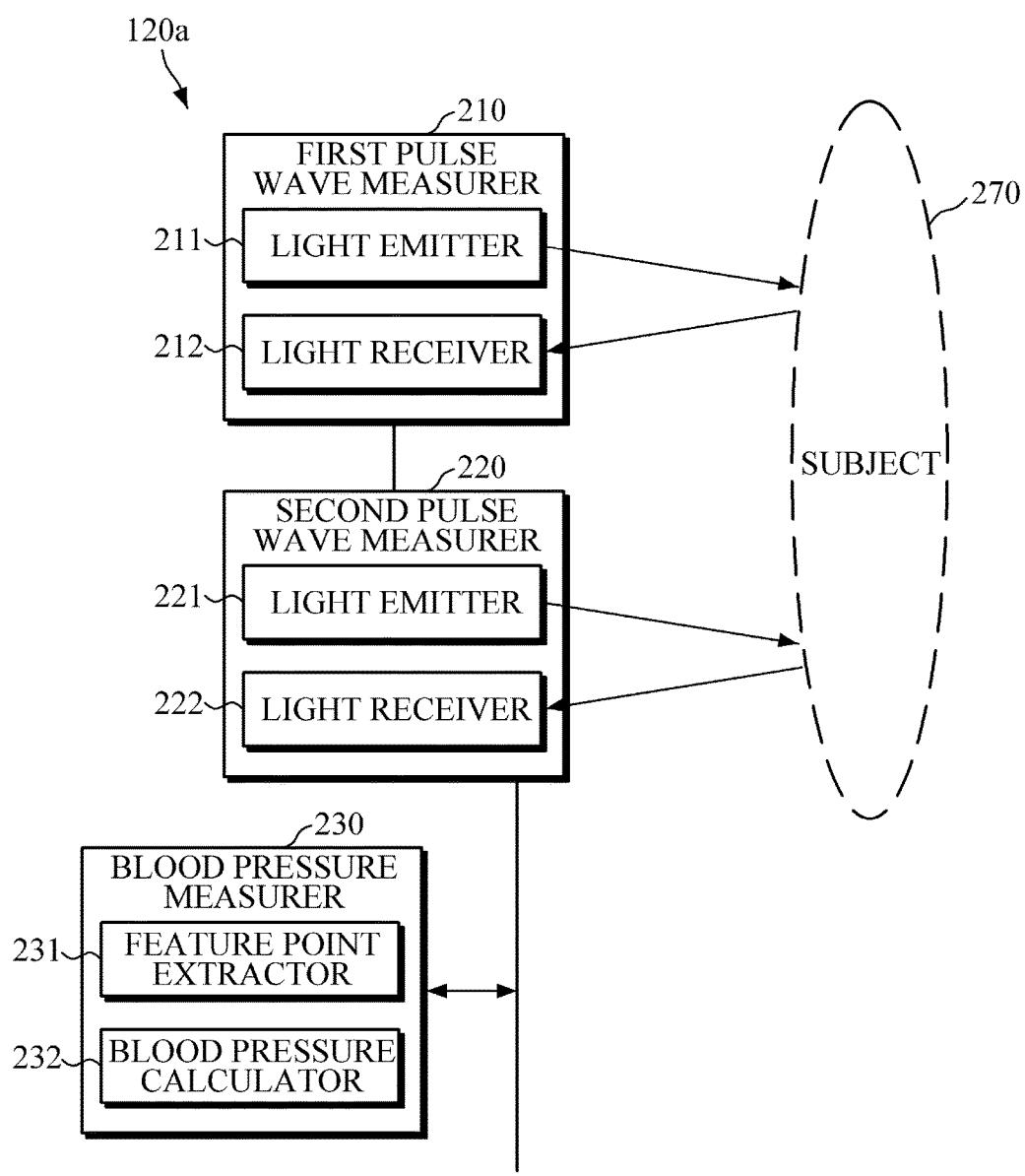
FIG. 2 is a block diagram illustrating a main body 120 according to an exemplary embodiment.

FIG. 2 is a block diagram illustrating a main body 120 according to an exemplary embodiment.

Referring to FIG. 2, a main body 120a includes a first pulse wave measurer 210, a second pulse wave measurer 220, and a blood pressure measurer 230.

The first pulse wave measurer 210 and the second pulse wave measurer 220 may measure pulse waves of a subject 270. As described above, the first pulse wave measurer 210 and the second pulse wave measurer 220 may be spaced apart. For example, the first pulse wave measurer 210 and the second pulse wave measurer 220 may be disposed on a left-end side and a right-end side of the bottom surface of the main body 120, and vice versa.

The first pulse wave measurer 210 may include a light emitter 211 and a light receiver 212. The second pulse wave measurer 220 may include a light emitter 221 and a light receiver 222. The light emitters 211 and 221 may emit light onto the subject 270. The emitted right may be diffused or reflected from the subject, and the light receivers 212 and 222 may detect the diffused or reflected light. The first pulse wave measurer 210 and the second pulse wave measurer 220 may acquire pulse waves from a detected optical signal.

In one exemplary embodiment, a light emitting diode (LED) or a laser diode may be used as the light emitters 211 and 221. A photo diode, a photo transistor (PTr), or a charge-couple device (CCD) may be used as the light receivers 212 and 222.

The subject 270 is a subject of which blood pressure is to be measured, and may be a body part that may contact or may be adjacent to the first pulse wave measurer 210 and the second pulse wave measurer 220 of the blood pressure measuring apparatus 100, or a body part of which pulse waves may be easily measured by using photoplethysmography (PPG). For example, the subject 270 may be an area on a wrist that is adjacent to the radial artery. In the case of measuring pulse waves on a position of the wrist over the radial artery, there may be relatively less external factors, such as the thickness of the skin tissue of the wrist, which may cause measurement errors. The radial artery is known to be a position where blood pressure may be measured more accurately than other arteries. However, the subject 270 is not limited thereto, and may be distal body portions, such as fingers and toes, which have a high density of blood vessels.

The blood pressure measurer 230 may measure blood pressure by analyzing pulse waves measured by the first pulse wave measurer 210 (hereinafter referred to as a first pulse wave) and pulse waves measured by the second pulse wave measurer 220 (hereinafter referred to as a second pulse wave). To this end, the blood pressure measurer 230 may include a feature point extractor 231 and a blood pressure calculator 232.

The feature point extractor 231 may extract a feature point from the first pulse wave (hereinafter referred to as a first feature point), and may extract a feature point corresponding to the first feature point from the second pulse wave (hereinafter referred to as a second feature point), in which the feature points may be a start point, a maximum point, a minimum point, and the like.

The blood pressure calculator 232 may calculate blood pressure based on the first feature point and the second feature point. For example, the blood pressure calculator 232 may calculate a pulse wave velocity based on the first feature point and the second feature point, and may calculate blood pressure based on the calculated pulse wave velocity and a blood pressure estimation equation. The blood pressure estimation equation defines a relationship between blood pressure and the pulse wave velocity, and may be stored in a database or in an external memory.

Figure 3:
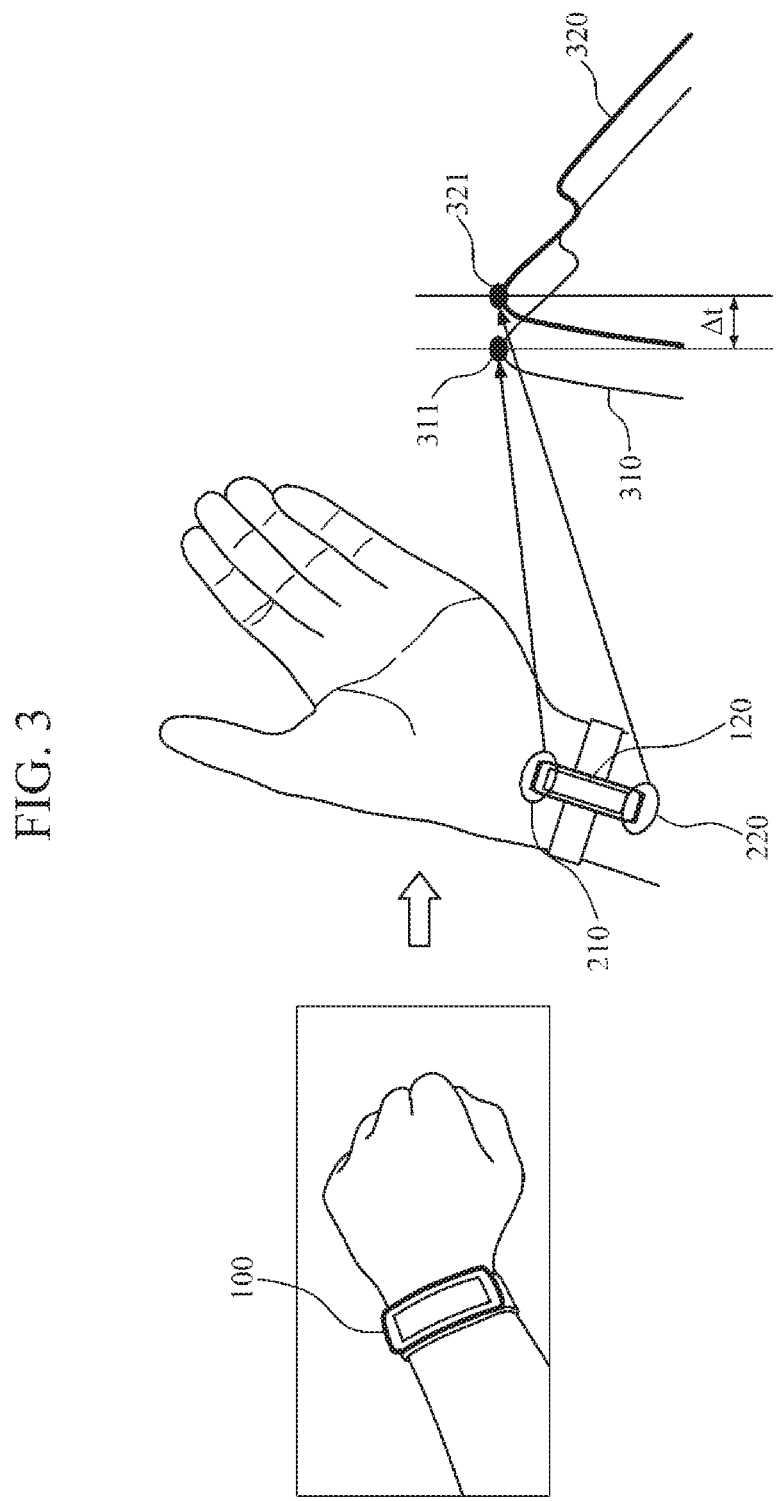
FIG. 3 is a diagram illustrating an example of applying a blood pressure measuring apparatus 100.

FIG. 3 is a diagram illustrating an example of applying a blood pressure measuring apparatus according to an exemplary embodiment.

Referring to FIGS. 2 and 3, the blood pressure apparatus 100 may be used as a wristwatch at ordinary time, but once a user positions the main body 120 of the blood pressure measuring device 100 over the radial artery of the wrist, rotates the main body 120 by 90 degrees, and inputs an instruction to measure blood pressure, the blood pressure measuring apparatus 100 may measure pulse waves by using the two pulse wave measurers 210 and 220 disposed on the bottom surface of the main body 120. A waveform 310 indicates the first pulse wave measured by the first pulse wave measurer 210, and a waveform 320 indicates the second pulse wave measured by the second pulse wave measurer 220.

The feature point extractor 231 extracts the first feature point 311 from the first pulse wave, and extracts the second feature point 321 corresponding to the first feature point 311 from the second pulse wave.

The blood pressure calculator 232 calculates a pulse wave velocity by calculating a time difference $\Delta t$ between the first feature point 311 and the second feature point 321, and by dividing a distance between the first pulse wave measurer 210 and the second pulse wave measurer 220 by the calculated time difference $\Delta t$.

Since the pulse wave velocity is increased when blood vessel elasticity is reduced, the pulse wave velocity may be a good indicator to show the blood vessel elasticity and a change in blood pressure, and may be used to establish a correlation between the pulse wave velocity and blood pressure.

The blood pressure calculator 232 may calculate blood pressure by using a blood pressure estimation equation that defines a relationship between the pulse wave velocity and blood pressure.

Figure 4:
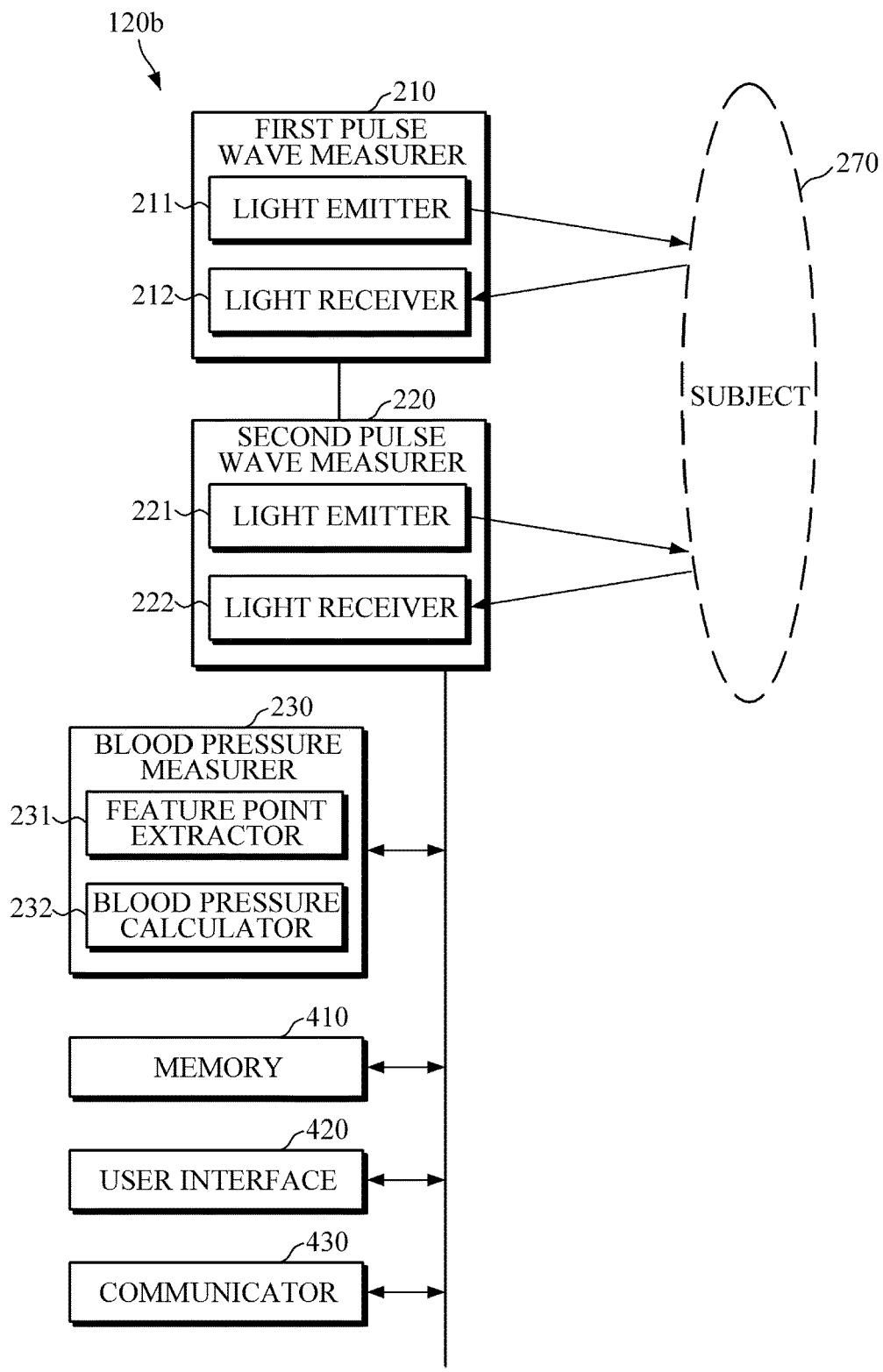
FIG. 4 is a block diagram illustrating the main body 120 according to another exemplary embodiment.

FIG. 4 is a block diagram illustrating the main body 120 according to another exemplary embodiment.

Referring to FIG. 4, when compared to the main body 120a illustrated in FIG. 2, a main body 120b may further include a memory 410, a user interface 420, and a communicator 430 selectively.

The memory 410 may store programs to process and control the blood pressure measurer 230, and may store input/output data. For example, the memory 410 may store programs for pulse wave analysis and blood pressure calculation performed by the blood pressure measurer 230, and/or information on a blood pressure estimation equation. Further, the memory 410 may store pulse wave measurement results of the pulse wave measurers 210 and 220. The blood pressure measurer 230 may read the pulse wave measurement results from the memory and process the results.

The memory 410 may include at least one storage medium among flash memory type, hard disk type, multimedia card micro type, card type memory (e.g., SD or XD memory, etc.), random access memory (RAM), static random access memory (SRAM), read-only memory (ROM), electrically erasable programmable read only memory (EEPROM), programmable read only memory (PROM), magnetic memory, magnetic disks, optical discs, and the like.

The user interface 420 is an interface between the blood pressure measuring apparatus 100 and a user, and/or an interface between the blood pressure measuring apparatus 100 and other external device, and may include an input and an output. The user may be a subject of which blood pressure is to be measured, i.e., the subject 270, but may be a concept wider than the subject 270.

Information for operating the blood pressure measuring apparatus 100 is input through the user interface 420, and measurement results of blood pressure may be output through the user interface 420. The user interface 420 may include, for example, a button, a connector, a keypad, a display, and the like, and may further include a sound output component or a vibration motor.

The communicator 430 may communicate with external devices. For example, the communicator 430 may transmit measurement results of blood pressure to an external device, or may receive various types of information useful for measuring blood pressure from an external device.

The external device may be medical equipment using information on the measured blood pressure, a printer to print out results, or a display to display information on the measured blood pressure. In addition, the external device may be a smartphone, a mobile phone, a personal digital assistant (PDA) device, a laptop computer, a personal computer (PC), and other mobile or non-mobile computing devices.

The communicator 430 may communicate with external devices by using Bluetooth communication, Bluetooth Low Energy communication, Near Field Communication (NFC), WLAN communication, Wi-Fi Direct (WFD) communication, Ultra Wideband (UWB) communication, Ant+ communication, Wi-Fi communication, Radio Frequency Identification (RFID) communication, and the like. However, the communicator 430 is merely illustrative, and is not limited thereto.

Figure 5:
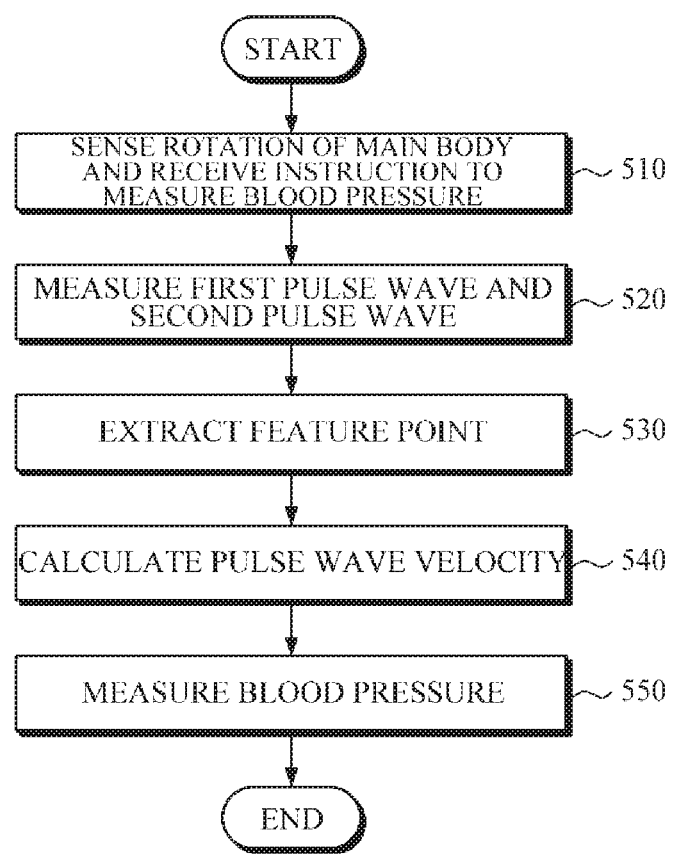
FIG. 5 is a flowchart illustrating a method of operating a blood pressure measuring apparatus 100 according to an exemplary embodiment.

FIG. 5 is a flowchart illustrating a method of operating a blood pressure measuring apparatus according to an exemplary embodiment.

Referring to FIG. 5, the blood pressure measuring apparatus 100 may sense rotation of the main body 120, and receives an instruction to measure blood pressure in operation 510. The blood pressure measuring apparatus 100 may sense a degree of rotation of the main body 120 in relation to the strap 110. For example, when the blood pressure measuring apparatus 100 determines that the degree of rotation is approximately 90 degrees and therefore the main body is perpendicular to the strap 110, the blood pressure measuring apparatus 100 may generate an instruction to measure the blood pressure. Alternatively, the instruction to measure the blood pressure may be input by a user after the main body 120 is rotated to be perpendicular to the strap 110.

The blood pressure apparatus 100 measures the first pulse wave at a first point by using the first pulse wave measurer 210, and measures the second pulse wave at a second point by using the second pulse wave measurer 220 in 520. For example, the blood pressure measuring apparatus 100 emits light on a subject by using the first pulse wave measurer 210, and senses light reflected from the subject 270 to measure the first pulse wave. The blood pressure measuring apparatus 100 emits light on the subject 270, and senses light reflected from the subject 270 to measure the second pulse wave.

In this case, the first pulse wave measurer 210 and the second pulse wave measurer 220 may be spaced apart from each other at a regular interval. For example, the first pulse wave measurer 210 and the second pulse wave measurer 220 may be disposed on both ends of the bottom surface of the main body 120.

The blood pressure measuring apparatus 100 extracts feature points by analyzing the first pulse wave and the second pulse wave in 530. For example, the blood pressure measuring apparatus 100 may extract the first feature point by analyzing the first pulse wave, and may extract the second feature point corresponding to the first feature point by analyzing the second pulse wave. The feature points may include a start point, a maximum point, a minimum point, and the like.

The blood pressure measuring apparatus 100 may calculate a pulse wave velocity based on the first feature point and the second feature point in 540. For example, the blood pressure measuring apparatus 100 may calculate the pulse wave velocity by calculating a time difference $\Delta t$ between the first feature point and the second feature point, and by dividing a distance between the first pulse wave measurer 210 and the second pulse wave measurer 220 by the calculated time difference $\Delta t$.

The blood pressure measuring apparatus 100 may estimate blood pressure by using the calculated pulse wave velocity and a blood pressure estimation equation.

Since pulse wave velocity is increased when blood vessel elasticity is reduced, the pulse wave velocity may be a good indicator to show the blood vessel elasticity and a change in blood pressure. The blood pressure estimation equation defines a relationship between blood pressure and the pulse wave velocity.

While not restricted thereto, an exemplary embodiment can be realized as a computer-readable code written on a computer-readable recording medium. Codes and code segments needed for realizing the present disclosure can be easily deduced by computer programmers of ordinary skill in the art. The computer-readable recording medium may be any type of recording device in which data is stored in a computer-readable manner. Examples of the computer-readable recording medium include a read-only memory (ROM), a random-access memory (RAM), a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A blood pressure measuring apparatus, comprising:
   a strap; and
   a main body that is rotatably connected to the strap, the main body comprising:
      a first pulse wave measurer configured to measure a first pulse wave using a first light emitter and a first light receiver;
      a second pulse wave measurer that is spaced apart from the first pulse wave measurer and is configured to measure a second pulse wave using a second light emitter and a second light receiver; and
      a processor configured to analyze the first pulse wave and the second pulse wave, and determine a blood pressure based on the analyzed first pulse wave and the analyzed second pulse wave,
   wherein the main body is configured to rotate from a first position in which a lengthwise direction of the main body is parallel to a lengthwise direction of the stray to a second position in which the lengthwise direction of the main body is perpendicular to the lengthwise direction of the strap, while the main body stays connected to the strap.

2. The apparatus of claim 1, wherein the main body is detachably connected to the strap.

3. The apparatus of claim 1, wherein the main body is configured to rotate in a range between 180 degrees and zero degree while the main body stays connected to the strap.

4. The apparatus of claim 1, wherein the first pulse wave measurer is disposed on a side end of a bottom surface of the main body, and the second pulse wave measurer is disposed on another side end of the bottom surface of the main body.

5. The apparatus of claim 1, wherein the blood pressure measuring apparatus is a wristwatch wearable device.

6. The apparatus of claim 1, wherein each of the first pulse wave measurer and the second pulse wave measurer is configured to emit light to a subject that reflects the light, and
   the first pulse wave measurer is configured to sense the light reflected from the subject to measure the first pulse wave, and
   the second pulse wave measurer is configured to sense the light reflected from the subject to measure the second pulse wave.

7. The apparatus of claim 1, wherein the processor comprises:
   a feature point extractor configured to extract a first feature point from the first pulse wave and a second feature point from the second pulse wave, the second feature point corresponding to the first feature point; and
   a blood pressure calculator configured to determine the blood pressure based on the first feature point and the second feature point.

8. The apparatus of claim 7, wherein the blood pressure calculator is further configured to determine a pulse wave velocity between the first feature point and the second feature point, and determine the blood pressure based on the determined pulse wave velocity.

9. The apparatus of claim 8, wherein the blood pressure calculator is further configured to determine the pulse wave velocity by determining a time difference between the first feature point and the second feature point, and by dividing a distance between the first pulse wave measurer and the second pulse wave measurer by the determined time difference.

* * * * *